(12) United States Patent
Tarquini et al.

(10) Patent No.: US 7,288,678 B2
(45) Date of Patent: *Oct. 30, 2007

(54) PROCESS FOR PREPARING TERBINAFINE BY USING PLATINUM AS CATALYST

(75) Inventors: Antonio Tarquini, Tortona (IT); Graziano Castaldi, Briona (IT); Gianluca Galdi, Genoa (IT); Pietro Allegrini, Milanese (IT)

(73) Assignee: Dipharma S.p.A., Mereto di Tomba (IT)

( * ) Notice: Subject to any disclaimer, the term of this patent is extended or adjusted under 35 U.S.C. 154(b) by 148 days.

This patent is subject to a terminal disclaimer.

(21) Appl. No.: 10/536,312

(22) PCT Filed: Nov. 21, 2003

(86) PCT No.: PCT/EP03/13124

§ 371 (c)(1),
(2), (4) Date: May 26, 2005

(87) PCT Pub. No.: WO2004/050604

PCT Pub. Date: Jun. 17, 2004

(65) Prior Publication Data

US 2006/0069164 A1 Mar. 30, 2006

(30) Foreign Application Priority Data

Nov. 29, 2002 (IT) .......................... MI2002A2534

(51) Int. Cl.
C07C 211/00 (2006.01)
C07C 211/21 (2006.01)
(52) U.S. Cl. ...................................... 564/387; 564/366
(58) Field of Classification Search ...................... None
See application file for complete search history.

(56) References Cited

U.S. PATENT DOCUMENTS 5,231,183 A 7/1993 Nakagawa et al.

FOREIGN PATENT DOCUMENTS

| EP | 0 421 302 | 4/1991 |
| EP | 1 236 709 | 9/2004 |
| WO | WO 01/77064 | 10/2001 |
| WO | WO 02/02503 | 1/2002 |

OTHER PUBLICATIONS

Database CAPLUS on STN, Acc. No. 1981:569006, STUTZ, EP 24587 (Mar. 11, 1981) (abstract).*
Alami et al., Journal of Organometallic Chemistry (2001), 624, p. 114-123.*
Alami M et al: "A Two-Step Synthesis of Terbinafine" Tetrahedron Letters, Elsevier Science Publishers, Amsterdam, NL, vol. 37, No. 1, 1996, pp. 57-58, XP004030473 ISSN: 0040-4039 the whole document.

* cited by examiner

*Primary Examiner*—Brian J. Davis
(74) *Attorney, Agent, or Firm*—Young & Thompson

(57) ABSTRACT

A process for the preparation of terbinafine, comprising the reaction of a compound of formula (II), or a salt thereof, wherein X is a leaving group, with tert-butylacetylene, in the presence of a platinum catalyst

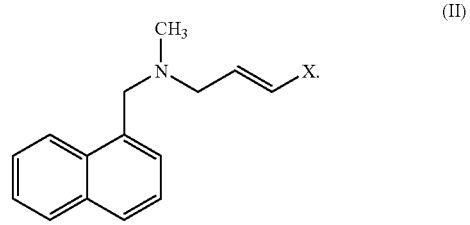

10 Claims, No Drawings

PROCESS FOR PREPARING TERBINAFINE BY USING PLATINUM AS CATALYST

FIELD OF THE INVENTION

The present invention belongs to the field of pharmaceutical chemistry and relates to a novel process for preparing terbinafine and the pharmaceutically acceptable salts thereof.

TECHNOLOGICAL BACKGROUND

Terbinafine, or (E)-N-(6,6-dimethyl-2-hepten-4-ynyl)-N-methyl-1-naphthalenemethanamine, is a known medicament with antifungal activity for topical use and has been first disclosed in EP 024587. The (E) stereoisomer of said compound is biologically active. In view of the interest of this product, various alternative processes for its production, more advantageous than those disclosed in EP 024587, have been developed, particularly those disclosed in EP 421302, WO 02/02503 and EP 1236709.

EP 421302 and WO 02/02503 disclose processes in which the last synthetic step comprises the reaction of N-(3-chloro-2-propenyl)-N-methyl-1-naphthalenemethanamine with tert-butylacetylene, in the presence of an organic amine and catalytic amounts of palladium salts and copper(I) iodide. Palladium compounds conventionally used for the coupling reaction known as "palladium catalyst-cross coupling reaction" are used as palladium catalysts. Examples of the palladium compounds reported in EP 421302 and WO 02/02503 comprise palladium-tertiary phosphine complexes, combinations of a palladium salt with a tertiary phosphine and a combination of a palladium complex with a tertiary phosphine. The processes described in said documents afford terbinafine in good yields but they have some remarkable drawbacks: for instance, the final product is contaminated by palladium and decomposition products of the palladium-phosphorous complexes, which have to be removed with cumbersome, expensive purification processes, for example by liquid column chromatography.

The process disclosed in EP 1236709 has overcome the drawbacks connected with the use of palladium catalysts, by reacting N-(3-chloro-2-propenyl) -N-methyl-1-naphthalenemethanamine with tert-butylacetylene in alkali medium in the presence of copper(I) salts only. This process affords terbinafine free from catalyst contaminations in good yield, but it requires long reaction times, which do not suitably meet the requirements for the industrial production on a large scale.

As a consequence, there is the need for alternative processes for the preparation of terbinafine on an industrial scale, which overcome the drawbacks of the known processes.

The inventors of the present invention have surprisingly found a novel process for the preparation of terbinafine, which can be carried out in comparatively short reaction times and affords a product free from catalyst contaminations and other reaction by-products, and moreover in significantly quantitative yield and improved stereoisomeric (E/Z) ratio.

DETAILED DISCLOSURE OF THE INVENTION

The present invention relates to a process for preparing terbinafine, or a pharmaceutically acceptable salt thereof, comprising reacting a compound of formula (II), or a salt thereof,

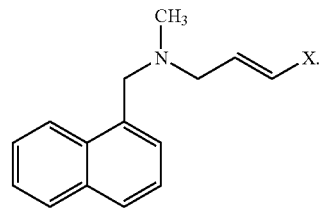

wherein X is a leaving group, with tert-butylacetylene, in the presence of a platinum catalyst.

The leaving group X is a conventional leaving group, for example a halogen atom, in particular chlorine, bromine or iodine, a perfluoroalkylsulfonic group, in particular perfluorooctylsulfonic or perfluorobutylsulfonic, or an an esterified hydroxy group, e.g. a —O-mesyl or —O-tosyl group.

A salt of a compound of formula (II) is a salt with an organic or inorganic acid and is a further object of the invention. Examples of salts of a compound of formula (II) are hydrochloride, hydrobromide, sulfate, fumarate, formate, acetate, propionate, tartrate, citrate, oxalate, malonate, maleate, methanesulfonate, paratoluenesulfonate or benzoate or a derivative thereof wherein the phenyl ring is optionally substituted with one or two groups independently selected from chlorine, bromine, iodine, hydroxy, nitro, $C_1$-$C_6$ alkyl and $C_1$-$C_6$ alkoxy. A preferred salt is N-(3-chloro-2-propenyl)-N-methyl-1-naphthalenemethanamine oxalate.

The reaction between a compound of formula (II), or a salt thereof, and tert-butylacetylene is carried out in an organic solvent, in the presence of a platinum catalyst and a basic agent. The same reaction can be carried out in the presence of additional amounts of a copper compound.

The platinum catalyst is platinum metal or a derivative thereof, for example platinum acetylacetonate, platinum bis(benzonitrile)dichloride, platinum oxide, a platinum halide, such as platinum chloride, bromide and iodide, or platinum acetate, in particular, platinum chloride or platinum metal, the latter preferably on an inert support, such as carbon, silica or alumina, preferably carbon. A particularly preferred example of catalyst is platinum metal on a carbon support, e.g. charcoal, with platinum content from about 1% to about 10%, preferably from about 5% to about 10%.

A copper compound is for example copper (I) chloride, copper (I) bromide, copper (I) iodide, copper acetate or copper (I) oxide, preferably copper (I) iodide.

The organic solvent can be an organic protic solvent, such as methanol or ethanol; a halogenated hydrocarbon, such as chloroform or dichloromethane; an aromatic hydrocarbon, such as benzene or toluene; an ether, such as diethyl ether, tetrahydrofuran or dioxane; or an organic aprotic solvent, such as dimethylformamide, dimethyl sulfoxide or acetonitrile.

The basic agent can be an organic or inorganic base. Examples of organic base are trimethylamine, triethylamine, pyridine, piperidine, butylamine, N,N-dimethylformamide and 4-dimethylaminopyridine, preferably piperidine or butylamine. Examples of inorganic base are sodium or potassium hydroxide, bicarbonate and carbonate.

The organic base itself, for example piperidine, pyridine or triethylamine, can act as the organic solvent when used in a large excess, typically in amounts approx. from 3 to 20 equivalents per equivalent of a compound of formula (II), or a salt thereof.

The coupling reaction between tert-butylacetylene and a compound of formula (II), or a salt thereof, can be carried out using stoichiometric amounts of the two reagents, or a tert-butylacetylene excess, for example approximately from 1 to 2, preferably approximately 1.3-1.6, equivalents of tert-butylacetylene per equivalent of a compound of formula (II), or a salt thereof.

The amount of platinum catalyst is preferably approximately equal to or lower than 10% molar with respect to a compound of formula (II), or a salt thereof, typically lower than approximately 3%-10% molar.

The amount of a copper compound is preferably a catalytic amount and its molar amount is usually twice the molar amount of platinum catalyst.

The reaction is typically carried out adding tert-butylacetylene to a dispersion of compound of formula (II), or a salt thereof, platinum catalyst and basic agent in the organic solvent, optionally also adding a copper compound as defined above. The reaction is carried out with stirring and preferably under inert atmosphere, for example under nitrogen atmosphere. When the organic base itself, for example piperidine, is used as the organic solvent, tert-butylacetylene is added to a dispersion of compound of formula (II), or a salt thereof, platinum catalyst and optionally copper compound in piperidine. The reaction temperature can range from about 0° C. to about 80° C., preferably from about 20° C. about 90° C., more preferably from about 30° C. to about 80° C. Reaction times approximately range about from 3 to 10 hours, preferably from 4 to 7 hours.

After completion of the reaction, terbinafine is recovered from the reaction mixture through a series of steps comprising:

a) treatment of the reaction mixture with a mixture of water and an organic solvent in which terbinafine is soluble, for example toluene;

b) separation of the platinum catalyst, when use of platinum metal catalyst on an inert support is made;

c) neutralization of the mixture by treatment with a suitable acid, for example hydrochloric acid; and d) separation of the organic phase containing terbinafine and evaporation of the organic solvent, to obtain crude terbinafine in very good yield.

A pharmaceutically acceptable salt of terbinafine is for example an addition salt with a mineral or organic acid, such as hydrochloric, sulfuric, nitric or malic acid. terbinafine can be converted into a pharmaceutically acceptable salt thereof by known methods, e.g. as reported in EP 1236709.

The process of the invention surprisingly provides terbinafine with enriched stereoisomeric E/Z ratio than the one of the starting compound of formula (II), thus it allows preparation of terbinafine as substantially pure (E)-form even starting from a compound of formula (II) wherein the E/Z ratio is lower than or equal to 95%. Moreover such terbinafine pure (E)-form is endowed with high purity, being in particular free from catalyst residues and other by-products. In particular, when the coupling reaction is carried out using a compound of formula (II) in a salified form, highly pure terbinafine (E)-form is already obtained at this step. Anyway, if the case, subsequent isolation of pure terbinafine pure (E)-form can be carried out according to known methods, for example in EP 1236709.

A further object of the invention is pure terbinafine, namely (E)-N-(6,6-dimethyl-2-hepten-4-ynyl)-N-methyl-1-naphthalenemethanamine, or a pharmaceutically acceptable salt thereof, in particular the hydrochloride, as pure (E)-form and free from catalyst residues, as obtainable by the process of the invention.

By "pure" is meant having a purity equal to or greater than 99.5%.

By "pure (E)-form" is meant having a stereoisomeric (E)-form purity equal to or greater than 99.5.

By "free from catalyst residues" is meant a residue amount in platinum catalyst and/or a copper compound lower than 1 p.p.m.

From what described above and from the results reported in the experimental section, it will be appreciated that the novel process for the preparation of terbinafine affords this product free from catalyst and by-products contaminants, and also in a significantly quantitative yield and with very good stereoisomeric (E/Z) ratio, in particular also as pure (E)-form, already at the step yielding crude terbinafine.

The process of the invention is particularly suitable for the industrial production of terbinafine, as reaction times are comparatively short and the platinum catalyst can be easily recovered quantitatively, thus remarkably decreasing production costs. Furthermore, the process requires no chromatographic purifications which are known to be time consuming, complex and hardly suitable for the industrial production.

Tert-butylacetylene and the compound of formula (II) are known products or can be prepared according to known methods, for example as reported in EP 421303. A salt of a compound of formula (II) can be obtained by salification of a compound of formula (II) with organic or inorganic acids according to known methods, for example as reported herein.

The following examples further illustrate the invention.

EXAMPLE 1

Preparation of Terbinafine

A 50 ml 3-necked round-bottom flask equipped with condenser, thermometer and magnetic stirrer, under nitrogen atmosphere, is loaded with 10 g of N-(3-chloro-2-propenyl)-N-methyl-1-naphthalenemethanamine (40.69 mmoles) (E/Z=80/20), 15.8 g of 10% Pt/C with 50% humidity (4.07 mmoles), 1.54 g of CuI (8.14 mmoles), 55.4 g of piperidine (651.1 mmoles) at room temperature. The mixture is heated under stirring to approx. 80° C. inner temperature for 30', then cooled to about 40° C. and 4.68 g of t-butylacetylene (56.96 mmoles) is dropped therein.

The reaction mixture is kept at this temperature for 4 hours, then cooled at room temperature and diluted with 80 ml of toluene and 60 ml of water. Stirring is continued for about 15', then the mixture is filtered through Celite® and filtration mother liquors are acidified under stirring with 61.9 g of 37% HCl (610.37 mmoles).

The phases are separated and the toluene phase is evaporated under vacuum at 50° C. to obtain 12.11 g of an oily residue consisting of 11.5 g of terbinafine (95% HPLC purity) corresponding to 97% molar yield. The resulting product has m.p. 193÷194° C. (E/Z=85/15) and the structure is consistent with $^1$HNMR and MS spectra.

$^1$HNMR (CDCl$_3$) δ (ppm): 1.23 (s, 9H); 2.60 (d, 3H); 3.72 (m, 2H); 4.65 (m, 2H); 5.85 (d, 1H); 6.34 (m, 1H); 7.52÷8.11 (m, 7H).

MS (EI 70 eV) m/e: 291, 276, 234, 196, 150, 141, 115.

EXAMPLE 2

Preparation of Terbinafine

A 50 ml 3-necked round-bottom flask equipped with condenser, thermometer and magnetic stirrer, under nitrogen atmosphere, is loaded with 2.05 g of N-(3-chloro-2-propenyl)-N-methyl-1-naphthalenemethanamine oxalate (6.1 mmoles) (E/Z=80/20), 2.38 g of 10% Pt/C with 50% humidity (0.7 mmoles), 0.26 g of CuI (1.4 mmoles), 7.8 g of piperidine (91.5 mmoles) at room temperature. The mixture is heated under stirring to approx. 80° C. inner temperature for 30', then cooled to about 40° C. and 1.02 g of t-butylacetylene (12.5 mmoles) is dropped therein.

The reaction mixture is kept at this temperature for 4 hours, then cooled at room temperature and diluted with 50 ml of toluene and 25 ml of water. Stirring is continued for about 15', then the mixture is filtered through Celites® and filtration mother liquors are acidified under stirring with 11.5 g of 37% HCl (116.7 mmoles).

The phases are separated and the toluene phase is evaporated under vacuum at 50° C. to obtain 1.76 g of an oily residue consisting of 1.70 g of terbinafine (96.5% HPLC purity) (5.86 mmoles) corresponding to 95.6% molar yield. The resulting product has m.p. 193÷195° C. (E/Z=88/12) and the structure is consistent with $^1$HNMR and MS spectra.

$^1$HNMR (CDCl$_3$) δ (ppm): 1.22 (s, 9H); 2.61 (d, 3H); 3.72 (m, 2H); 4.65 (m, 2H); 5.87 (d, 1H); 6.34 (m, 1H); 7.52÷8.10 (m, 7H).

MS (EI 70 eV) m/e: 291, 276, 234, 196, 150, 141, 115.

EXAMPLE 3

Preparation of Terbinafine

A 100 ml 3-necked round-bottom flask equipped with condenser, thermometer and magnetic stirrer, under nitrogen atmosphere, is loaded with 10 g of N-(3-chloro-2-propenyl)-N-methyl-1-naphthalenemethanamine (40.69 mmoles) (E/Z=80/20), 15.8 g of 10% Pt/C with 50% humidity (4.07 mmoles), 1.54 g of CuI (8.14 mmoles), 3.24 g of pyridine (41.0 mmoles) and 40 ml of toluene, at room temperature. The mixture is heated under stirring to approx. 80° C. inner temperature for 30', then cooled to about 40° C. and 4.68 g of t-butylacetylene (56.96 mmoles) is dropped therein.

The reaction mixture is kept at this temperature for 6 hours, then cooled at room temperature and diluted with 40 ml of water. Stirring is continued for about 15', then the mixture is filtered through Celite® and filtration mother liquors are acidified under stirring with 4.5 g of 37% HCl (0.31 mmoles).

The phases are separated and the toluene phase is evaporated under vacuum at 50° C. to obtain 11.9 g of an oily residue consisting of 11.3 g of terbinafine (94.9% HPLC purity) corresponding to 95% molar yield. The resulting product has m.p. 193÷194° C. (E/Z=83/17) and the structure is consistent with $^1$HNMR and MS spectra.

$^1$HNMR (CDCl$_3$) δ (ppm): 1.23 (s, 9H); 2.62 (d, 3H); 3.72 (m, 2H); 4.65 (m, 2H); 5.85 (d, 1H); 6.33 (m, 1H); 7.52÷8.11 (m, 7H).

MS (EI 70 eV) m/e: 291, 276, 234, 196, 150, 141, 115.

EXAMPLE 4

Preparation of Terbinafine

A 50 ml 3-necked round-bottom flask equipped with condenser, thermometer and magnetic stirrer, under nitrogen atmosphere, is loaded with 10 g of N-(3-chloro-2-propenyl)-N-methyl-1-naphthalenemethanamine (40.69 mmoles) (E/Z=80/20), 1 g of PtCl$_2$ (3.76 mmoles), 1.54 g of CuI (8.14 mmoles), 55.4 g of piperidine (650.6 mmoles) at room temperature. The mixture is heated under stirring to approx. 80° C. inner temperature for 30', then cooled to about 40° C. and 4.68 g of t-butylacetylene (56.96 mmoles) is dropped therein.

The reaction mixture is kept at this temperature for 4 hours, then cooled at r.t. and diluted with 40 ml of toluene and 80 ml of water. Stirring is continued for about 15', then the mixture is filtered through Celite® and filtration mother liquors are acidified under stirring with 56 g of 37% HCl (570 mmoles).

The phases are separated and the toluene phase is evaporated under vacuum at 50° C. to obtain 13.0 g of an oily residue consisting of 11.5 g of terbinafine (88% HPLC purity) (39.4 mmoles) corresponding to 96.9% molar yield. The resulting product has m.p. 193÷194° C. (E/Z=85/15) and the structure is consistent with $^1$HNMR and MS spectra.

$^1$HNMR (CDCl$_3$) δ (ppm): 1.23 (s, 9H); 2.60 (d, 3H); 3.72 (m, 2H); 4.65 (m, 2H); 5.85 (d, 1H); 6.34 (m, 1H); 7.52÷8.11 (m, 7H).

MS (EI 70 eV) m/e: 291, 276, 234, 196, 150, 141, 115.

EXAMPLE 5

Preparation of N-(3-chloro-2-propenyl)-N-methyl-1-naphthalenemethanamine oxalate A 500 ml 4-necked round-bottom flask equipped with thermometer and magnetic stirrer, under nitrogen atmosphere, is loaded with 80 g of N-(3-chloro-2-propenyl)-N-methyl-1-naphthalenemethanamine (325 mmoles) (E/Z=80/20) and 317 g of methanol at room temperature. The resulting solution is added with 29.3 g of oxalic acid (325 mmoles), keeping stirring for 15', then the precipitate is filtered and the product is washed with methanol on the filter. 94.0 g of N-(3-chloro-2-propenyl)-N-methyl-1-naphthalene-methanamine oxalate (279.9 mmoles) are obtained, 86% (E/Z=80/20) molar yield.

$^1$HNMR (DMSO-d$_6$) δ (ppm): 2.33 (s, 3H); 3.44 (d, 2H); 4.23 (s, 2H); 6.18 (m, 1H); 6.57 (d, 1H); 7.45÷8.25 (m, 7H).

$^{13}$CNMR (DMSO-d$_6$) δ (ppm): 163.55; 134.15; 132.56; 131.31; 129.73; 129.22; 128.08; 127.06; 126.68; 126.0; 124.93; 124.11, 57.53; 56.24.

EXAMPLE 6

Preparation of Terbinafine

A 50 ml 3-necked round-bottom flask equipped with condenser, thermometer and magnetic stirrer, under nitrogen atmosphere, is loaded with 3 g of N-(3-chloro-2-propenyl)-N-methyl-1-naphthalenemethanamine (12.0 mmoles) (E/Z=98/2), 0.27 g of Pt/C 10% (about 50% humidity) (0.069 mmoles), 0.027 g of CuI (0.14 mmoles), 3.11 g of piperidine (36 mmoles) at room temperature. The mixture is heated under stirring to approx. 80° C. inner temperature for 30', then cooled to about 40° C. and 1.29 g of t-butylacetylene (16 mmoles) is dropped therein.

The reaction mixture is heated at 80° C. and is kept in these conditions for 3 hours, then is cooled at r.t. and diluted with 40 ml of toluene and 80 ml of water. Stirring is continued for about 15', then the mixture is filtered through Celite® and filtration mother liquors are acidified under stirring with 3.1 g of 37% HCl (31.6 mmoles).

The phases are separated and the toluene phase is evaporated under vacuum at 50° C. to obtain 3.60 g of an oily residue consisting of 3.42 g of terbinafine (99.5% HPLC purity) (11.76 mmoles) corresponding to 98% molar yield. The resulting product has m.p. 193÷194° C. (E/Z=99.5:0.5), a content of catalyst residues lower than 1 p.p.m. and the structure is consistent with $^1$HNMR and MS spectra.

$^1$HNMR (CDCl$_3$) δ (ppm): 1.23 (s, 0.9H); 2.60 (d, 3H); 3.72 (m, 2H); 4.65 (m, 2H); 5.85 (d, 1H); 6.34 (m, 1H); 7.52÷8.11 (m, 7H).

MS (EI 70 eV) m/e: 291, 276, 234, 196, 150, 141, 115.

EXAMPLE 7

Terbinafine Hydrochloride

Terbinafine as obtained according to one of the above examples is reacted in acetone with a stoichiometric amount of 37% molar hydrochloric acid. Crystallization is obtained by seeding with pure terbinafine hydrochloride, cooling to −10° C. After one hour, the mixture is filtered and the solid is washed with acetone, then dried to obtain pure terbinafine hydrochloride as a white solid having 99.9% HPLC purity (E/Z=100:0) and a content of catalyst residues lower than 1 p.p.m.

What is claimed is:

1. A process for the preparation of terbinafine, or a pharmaceutically acceptable salt thereof, comprising reacting a compound of formula (II), or a salt thereof,

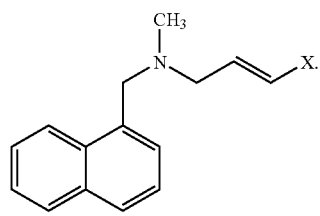

(II)

wherein X is a leaving group,
with tert-butylacetylene, in the presence of a platinum catalyst.

2. The process as claimed in claim 1, wherein the platinum catalyst is selected from the group consisting of platinum metal, platinum acetylacetonate, platinum bis(benzonitrile)dichloride, platinum oxide, platinum halide and platinum acetate.

3. The process as claimed in claim 1, wherein said reaction is carried out in an organic solvent, in the presence of a basic agent and a catalytic amount of a copper compound.

4. The process according to claim 3, wherein the copper compound is copper (I) chloride, copper (I) bromide, copper (I) iodide, copper acetate or copper (I) oxide.

5. The process according to claim 3, wherein the organic solvent is the basic agent itself.

6. The process as claimed in claim 5, wherein the basic agent is an organic or inorganic base.

7. The process according to claim 1, wherein the reaction is carried out in the presence of platinum chloride or platinum metal on an inert support; in the presence of a catalytic amount of copper (I) iodide, in the presence of a basic agent.

8. The process according to claim 7, wherein the molar amount of copper (I) iodide is twice the molar amount of platinum catalyst.

9. A compound of formula (II),

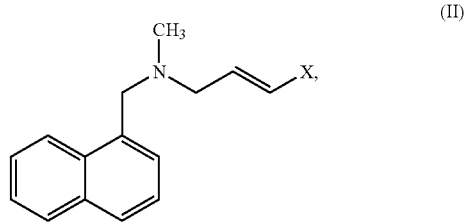

(II)

wherein X is a leaving group,
in the form of an organic or inorganic acid addition salt thereof.

10. The process as claimed in claim 2, wherein said reaction is carried out in an organic solvent, in the presence of a basic agent and a catalytic amount of a copper compound.

* * * * *